United States Patent [19]

Li et al.

[11] Patent Number: 5,679,523

[45] Date of Patent: Oct. 21, 1997

[54] METHOD FOR CONCURRENT DISRUPTION OF EXPRESSION OF MULTIPLE ALLELES OF MAMMALIAN GENES

[75] Inventors: Limin Li; Stanley N. Cohen, both of Stanford, Calif.

[73] Assignee: The Board of Trustees of the Leland Stanford Junior University, Palo Alto, Calif.

[21] Appl. No.: 585,758

[22] Filed: Jan. 16, 1996

Related U.S. Application Data

[60] Provisional application No. 60/006,856 Nov. 16, 1995.

[51] Int. Cl.$^6$ ............................. C12Q 1/68; C12N 15/00; C07H 21/04
[52] U.S. Cl. ..................... 435/6; 435/172.3; 435/320.1; 536/23.2; 536/24.5
[58] Field of Search ..................... 435/6, 172.3, 320.1; 536/23.2, 24.5

[56] References Cited

PUBLICATIONS

Baim et al., "A Chimeric Mammalian Transactivator Based on the lac Repressor that is Regulated by Temperature and Isopropyl β-D-thiogalactopyranoside," PNAS USA (1991), 88:5072–5076.

Lemke, "The Molecular Genetics of Myelination: An Update," GLIA (1993), 7:263–271.

Gossen et al., "Transcriptional Activation by Tetracyclines in Mammalian Cells," Science (1995), 268:1766–1769.

Stokes et al., "The Partial 3'–Conserved Segment Duplications in the Inegrons In6 from pSa and In7 from pDGO100 Have a Common Origin," Plasmid (1993), 30:39–50.

Kamano et al., "Effects of the Antisense v–myb' Expression on K562 Human Leukemia Cell Proliferation and Differentiation," Leukemia Research (1990), 14:831–839.

Baubonis and Sauer, "Genomic Targeting with Purified Cre Recombinase," Nucleic Acids Research (1993), 21:2025–2029.

Craig, "The Mechanism of Conservative Site–Specific Recombination," Annu. Rev. Genet. (1988), 22:77–105.

van der Krol et al., "Modulation of Eukaryotic Gene Expression by Complementary RNA or DNA Sequences," BioTechniques (1988), 6:958–976.

Katsuki et al., "Conversion of Normal Behavior to Shiverer by Myelin Basic Protein Antisense cDNA in Transgenic Mice," Science (1988), 593:595.

Owens and Boyd, "Expressing Antisense Po RNA in Schwann Cells Perturbs Myelination," Development (1991), 112:639–649.

Owens and Bunge, "Schwann Cells Infected with a Recombinant Retrovirus Expressing Myelin–Associated Glycoprotein Antisense RNA Do Not Form Myelin," Neuron (1991), 7:565–575.

Giese et al., "Mouse $P_o$ Gene Disruption Leads to Hypomyelination, Abnormal Expression of Recognition Molecules, and Degeneration of Myelin and Axons," Cell (1992), 71:565–576.

*Primary Examiner*—James Ketter
*Assistant Examiner*—John S. Brusca
*Attorney, Agent, or Firm*—Pamela J. Sherwood; Fish & Richardson P.C.

[57] ABSTRACT

Methods are provided for identifying a gene at a random chromosomal locus in the genome of a mammalian cell. The method involves inactivating one copy of the gene by integrating one DNA construct (knockout construct) in that gene copy. The knockout construct includes a positive selection marker region sequence and, in a 5' direction from the selection marker region sequence, a transcription initiation region sequence responsive to a transactivation factor, said transcription initiation region oriented for antisense RNA transcription in the direction away from the selection marker region sequence. The second copy of the gene is inactivated by transforming the cells with a second DNA construct (transactivation construct) containing a gene sequence for the transactivation factor which initiates antisense RNA transcription extending from the knockout construct into the chromosomal locus flanking the knockout construct at its 5' end. Inactivation of both gene copies may result in a change in cell phenotype distinguishable from the wild-type phenotype. Optionally, the wild-type phenotype can be regained by introducing a third construct that can inhibit antisense RNA transcription.

23 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1448 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 61..1203

( x i ) SEQUENCE DESCRIPTION: SEQ ID NO:1:

```
CCCCTCTGCC TGTGGGGACG GAGGAGCGCG CCATGGCTGT CCGAGAGTCA GCTGAAGAAG          60

ATG ATG TCC AAG TAC AAA TAT AGA GAT CTA ACC GTC CGT CAA ACT GTC          108
Met Met Ser Lys Tyr Lys Tyr Arg Asp Leu Thr Val Arg Gln Thr Val
 1               5                  10                  15

AAT GTC ATC GCT ATG TAC AAA GAT CTC AAA CCT GTA TTG GAT TCA TAT          156
Asn Val Ile Ala Met Tyr Lys Asp Leu Lys Pro Val Leu Asp Ser Tyr
```

```
                        20                         25                              30
GTT  TTT  AAT  GAT  GGC  AGT  TCC  AGG  GAG  CTG  GTG  AAC  CTC  ACT  GGT  ACA      204
Val  Phe  Asn  Asp  Gly  Ser  Ser  Arg  Glu  Leu  Val  Asn  Leu  Thr  Gly  Thr
          35                       40                      45

ATC  CCA  GTG  CGT  TAT  CGA  GGT  AAT  ATA  TAT  AAT  ATT  CCA  ATA  TGC  CTG      252
Ile  Pro  Val  Arg  Tyr  Arg  Gly  Asn  Ile  Tyr  Asn  Ile  Pro  Ile  Cys  Leu
          50                       55                      60

TGG  CTG  CTG  GAC  ACA  TAC  CCA  TAT  AAC  CCC  CCT  ATC  TGT  TTT  GTT  AAG      300
Trp  Leu  Leu  Asp  Thr  Tyr  Pro  Tyr  Asn  Pro  Pro  Ile  Cys  Phe  Val  Lys
65                       70                      75                          80

CCT  ACT  AGT  TCA  ATG  ACT  ATT  AAA  ACA  GGA  AAG  CAT  GTG  GAT  GCA  AAT      348
Pro  Thr  Ser  Ser  Met  Thr  Ile  Lys  Thr  Gly  Lys  His  Val  Asp  Ala  Asn
                    85                       90                          95

GGG  AAA  ATC  TAC  CTA  CCT  TAT  CTA  CAT  GAC  TGG  AAA  CAT  CCA  CGG  TCA      396
Gly  Lys  Ile  Tyr  Leu  Pro  Tyr  Leu  His  Asp  Trp  Lys  His  Pro  Arg  Ser
               100                      105                     110

GAG  TTG  CTG  GAG  CTT  ATT  CAA  ATC  ATG  ATT  GTG  ATA  TTT  GGA  GAG  GAG      444
Glu  Leu  Leu  Glu  Leu  Ile  Gln  Ile  Met  Ile  Val  Ile  Phe  Gly  Glu  Glu
               115                      120                     125

CCT  CCA  GTG  TTC  TCC  CGG  CCT  ACT  GTT  TCT  GCA  TCC  TAC  CCA  CCA  TAC      492
Pro  Pro  Val  Phe  Ser  Arg  Pro  Thr  Val  Ser  Ala  Ser  Tyr  Pro  Pro  Tyr
          130                      135                     140

ACA  GCA  ACA  GGG  CCA  CCA  AAT  ACC  TCC  TAC  ATG  CCA  GGC  ATG  CCA  AGT      540
Thr  Ala  Thr  Gly  Pro  Pro  Asn  Thr  Ser  Tyr  Met  Pro  Gly  Met  Pro  Ser
145                      150                     155                         160

GGA  ATC  TCT  GCA  TAT  CCA  TCT  GGA  TAC  CCT  CCC  AAC  CCC  AGT  GGT  TAT      588
Gly  Ile  Ser  Ala  Tyr  Pro  Ser  Gly  Tyr  Pro  Pro  Asn  Pro  Ser  Gly  Tyr
                    165                      170                         175

CCT  GGC  TGT  CCT  TAC  CCA  CCT  GCT  GGC  CCA  TAC  CCT  GCC  ACA  ACA  AGC      636
Pro  Gly  Cys  Pro  Tyr  Pro  Pro  Ala  Gly  Pro  Tyr  Pro  Ala  Thr  Thr  Ser
               180                      185                     190

TCA  CAG  TAC  CCT  TCC  CAG  CCT  CCT  GTG  ACC  ACT  GTT  GGT  CCC  AGC  AGA      684
Ser  Gln  Tyr  Pro  Ser  Gln  Pro  Pro  Val  Thr  Thr  Val  Gly  Pro  Ser  Arg
          195                      200                     205

GAT  GGC  ACA  ATC  AGT  GAG  GAC  ACT  ATC  CGT  GCA  TCT  CTC  ATC  TCA  GCA      732
Asp  Gly  Thr  Ile  Ser  Glu  Asp  Thr  Ile  Arg  Ala  Ser  Leu  Ile  Ser  Ala
          210                      215                     220

GTC  AGT  GAC  AAA  CTG  AGA  TGG  CGG  ATG  AAG  GAG  GAA  ATG  GAT  GGT  GCC      780
Val  Ser  Asp  Lys  Leu  Arg  Trp  Arg  Met  Lys  Glu  Glu  Met  Asp  Gly  Ala
225                      230                     235                         240

CAG  GCA  GAG  CTT  AAT  GCC  TTG  AAA  CGA  ACA  GAG  GAA  GAT  CTG  AAA  AAA      828
Gln  Ala  Glu  Leu  Asn  Ala  Leu  Lys  Arg  Thr  Glu  Glu  Asp  Leu  Lys  Lys
                    245                      250                         255

GGC  CAC  CAG  AAA  CTG  GAA  GAG  ATG  GTC  ACC  CGC  TTA  GAT  CAA  GAA  GTA      876
Gly  His  Gln  Lys  Leu  Glu  Glu  Met  Val  Thr  Arg  Leu  Asp  Gln  Glu  Val
               260                      265                     270

GCT  GAA  GTT  GAT  AAA  AAC  ATA  GAA  CTT  TTG  AAA  AAG  AAG  GAT  GAA  GAA      924
Ala  Glu  Val  Asp  Lys  Asn  Ile  Glu  Leu  Leu  Lys  Lys  Lys  Asp  Glu  Glu
          275                      280                     285

CTA  AGT  TCT  GCT  CTG  GAG  AAA  ATG  GAA  AAT  CAA  TCT  GAA  AAT  AAT  GAT      972
Leu  Ser  Ser  Ala  Leu  Glu  Lys  Met  Glu  Asn  Gln  Ser  Glu  Asn  Asn  Asp
          290                      295                     300

ATT  GAT  GAA  GTT  ATC  ATT  CCC  ACA  GCC  CCA  CTG  TAT  AAA  CAG  ATT  CTA     1020
Ile  Asp  Glu  Val  Ile  Ile  Pro  Thr  Ala  Pro  Leu  Tyr  Lys  Gln  Ile  Leu
305                      310                     315                         320

AAT  CTG  TAT  GCA  GAG  GAA  AAT  GCT  ATT  GAA  GAC  ACT  ATC  TTT  TAC  CTT     1068
Asn  Leu  Tyr  Ala  Glu  Glu  Asn  Ala  Ile  Glu  Asp  Thr  Ile  Phe  Tyr  Leu
                    325                      330                         335

GGA  GAA  GCT  TTG  CGG  CGG  GGA  GTC  ATA  GAC  CTG  GAT  GTG  TTC  CTG  AAA     1116
Gly  Glu  Ala  Leu  Arg  Arg  Gly  Val  Ile  Asp  Leu  Asp  Val  Phe  Leu  Lys
```

|   |   |   |   |   | 340 |   |   |   | 345 |   |   |   | 350 |   |   |   |
|---|---|---|---|---|---|---|---|---|---|---|---|---|---|---|---|---|
| CAC | GTC | CGC | CTC | CTG | TCC | CGT | AAA | CAG | TTC | CAG | CTA | AGG | GCA | CTA | ATG | 1164 |
| His | Val | Arg | Leu | Leu | Ser | Arg | Lys | Gln | Phe | Gln | Leu | Arg | Ala | Leu | Met |   |
|   |   | 355 |   |   |   |   | 360 |   |   |   |   | 365 |   |   |   |   |
| CAA | AAG | GCA | AGG | AAG | ACT | GCG | GGC | CTT | AGT | GAC | CTC | TAC | TGACATGTGC |   |   | 1213 |
| Gln | Lys | Ala | Arg | Lys | Thr | Ala | Gly | Leu | Ser | Asp | Leu | Tyr |   |   |   |   |
|   | 370 |   |   |   |   | 375 |   |   |   |   | 380 |   |   |   |   |   |

| TGTCAGCTGG | AGACCGACCT | CTCCGTAAAG | CATTCTTTTC | TTCTTCTTTT | TCTCATCAGT | 1273 |
|---|---|---|---|---|---|---|
| AGAACCCACA | ATAAGTTATT | GCAGTTATC | ATTCAAGTGT | TAAATATTTT | GAATCAATAA | 1333 |
| TATATTTTCT | GTTTCCTTTG | GGTAAAAACT | GGCTTTTATT | AATGCACTTT | CTACCCTCTG | 1393 |
| TAAGCGTCTG | TGCTGTGCTG | GGACTGACTG | GGCTAAATAA | AATTGTTGC | ATAAA | 1448 |

( 2 ) INFORMATION FOR SEQ ID NO:2:

( i ) SEQUENCE CHARACTERISTICS:
        ( A ) LENGTH: 381 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Met Ser Lys Tyr Lys Tyr Arg Asp Leu Thr Val Arg Gln Thr Val
 1               5                  10                  15

Asn Val Ile Ala Met Tyr Lys Asp Leu Lys Pro Val Leu Asp Ser Tyr
             20                  25                  30

Val Phe Asn Asp Gly Ser Ser Arg Glu Leu Val Asn Leu Thr Gly Thr
         35                  40                  45

Ile Pro Val Arg Tyr Arg Gly Asn Ile Tyr Asn Ile Pro Ile Cys Leu
     50                  55                  60

Trp Leu Leu Asp Thr Tyr Pro Tyr Asn Pro Pro Ile Cys Phe Val Lys
 65                  70                  75                  80

Pro Thr Ser Ser Met Thr Ile Lys Thr Gly Lys His Val Asp Ala Asn
                 85                  90                  95

Gly Lys Ile Tyr Leu Pro Tyr Leu His Asp Trp Lys His Pro Arg Ser
                100                 105                 110

Glu Leu Leu Glu Leu Ile Gln Ile Met Ile Val Ile Phe Gly Glu Glu
            115                 120                 125

Pro Pro Val Phe Ser Arg Pro Thr Val Ser Ala Ser Tyr Pro Pro Tyr
        130                 135                 140

Thr Ala Thr Gly Pro Pro Asn Thr Ser Tyr Met Pro Gly Met Pro Ser
145                 150                 155                 160

Gly Ile Ser Ala Tyr Pro Ser Gly Tyr Pro Pro Asn Pro Ser Gly Tyr
                165                 170                 175

Pro Gly Cys Pro Tyr Pro Pro Ala Gly Pro Tyr Pro Ala Thr Thr Ser
                180                 185                 190

Ser Gln Tyr Pro Ser Gln Pro Val Thr Thr Val Gly Pro Ser Arg
            195                 200                 205

Asp Gly Thr Ile Ser Glu Asp Thr Ile Arg Ala Ser Leu Ile Ser Ala
210                 215                 220

Val Ser Asp Lys Leu Arg Trp Arg Met Lys Glu Met Asp Gly Ala
225                 230                 235                 240

Gln Ala Glu Leu Asn Ala Leu Lys Arg Thr Glu Glu Asp Leu Lys Lys
                245                 250                 255

Gly His Gln Lys Leu Glu Glu Met Val Thr Arg Leu Asp Gln Glu Val
            260                 265                 270
```

| | | | | | | | | | | | | |
|---|---|---|---|---|---|---|---|---|---|---|---|---|
| Ala | Glu | Val | Asp | Lys | Asn | Ile | Glu | Leu | Leu | Lys | Lys | Asp | Glu | Glu |
| | 275 | | | | 280 | | | | | 285 | | |
| Leu | Ser | Ser | Ala | Leu | Glu | Lys | Met | Glu | Asn | Gln | Ser | Glu | Asn | Asn | Asp |
| | 290 | | | | | 295 | | | | 300 | | |
| Ile | Asp | Glu | Val | Ile | Ile | Pro | Thr | Ala | Pro | Leu | Tyr | Lys | Gln | Ile | Leu |
| 305 | | | | 310 | | | | | 315 | | | | 320 |
| Asn | Leu | Tyr | Ala | Glu | Glu | Asn | Ala | Ile | Glu | Asp | Thr | Ile | Phe | Tyr | Leu |
| | | | 325 | | | | | 330 | | | | | 335 |
| Gly | Glu | Ala | Leu | Arg | Arg | Gly | Val | Ile | Asp | Leu | Asp | Val | Phe | Leu | Lys |
| | | | 340 | | | | | 345 | | | | 350 | |
| His | Val | Arg | Leu | Leu | Ser | Arg | Lys | Gln | Phe | Gln | Leu | Arg | Ala | Leu | Met |
| | | 355 | | | | | 360 | | | | | 365 | |
| Gln | Lys | Ala | Arg | Lys | Thr | Ala | Gly | Leu | Ser | Asp | Leu | Tyr | | | |
| | 370 | | | | | 375 | | | | 380 | | |

( 2 ) INFORMATION FOR SEQ ID NO:3:

( i ) SEQUENCE CHARACTERISTICS:
        ( A ) LENGTH: 1494 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 120..1259

( x i ) SEQUENCE DESCRIPTION: SEQ ID NO:3:

| | | | | | |
|---|---|---|---|---|---|
| GAAGGGGGTG | TGCGATTGTG | TGGGACGGTC | TGGGGCAGCC | ACAGCGGCTG | ACCNCNTNGC | 60 |
| CTGCGGGGAA | GGGAGTCGCC | AGGGCCCGTC | ATCGGGTGTC | GGAGAGCCAG | CTCAAGAAAA | 120 |
| TGGTGTCCAA | GTACAAATAC | AGAGACCTAA | CTGTACGTGA | AACTGTCAAT | GTTATTACTC | 180 |
| TATACAAAGA | TCTCAAACCT | GTTTTGGATT | CATATGTTTT | TAACGATGGC | AGTTCCAGGG | 240 |
| AACTAATGAA | CCTCACTGGA | ACAATCCCTG | TGCCTTATAG | AGGTAATACA | TACAATATTC | 300 |
| CAATATGCCT | ATGGCTACTG | GACACATACC | CATATAATCC | CCTATCTGT | TTTGTTAAGC | 360 |
| CTACTAGTTC | AATGACTATT | AAAACAGGAA | AGCATGTTGA | TGCAAATGGG | AAGATATATC | 420 |
| TTCCTTATCT | ACATGAATGG | AAACACCCAC | AGTCAGACTT | GTTGGGCTT | ATTCAGGTCA | 480 |
| TGATTGTGGT | ATTTGGAGAT | GAACCTCCAG | TCTTCTCTCG | TCCTATTTCG | GCATCCTATC | 540 |
| CGCCATACCA | GGCAACGGGG | CCACCAAATA | CTTCCTACAT | GCCAGGCATG | CCAGGTGGAA | 600 |
| TCTCTCCATA | CCCATCCGGA | TACCCTCCCA | ATCCCAGTGG | TTACCCAGGC | TGTCCTTACC | 660 |
| CACCTGGTGG | TCCATATCCT | GCCACAACAA | GTTCTCAGTA | CCCTTCTCAG | CCTCCTGTGA | 720 |
| CCACTGTTGG | TCCCAGTAGG | GATGGCACAA | TCAGCGAGGA | CACCATCCGA | GCCTCTCTCA | 780 |
| TCTCTGCGGT | CAGTGACAAA | CTGAGATGGC | GGATGAAGGA | GGAAATGGAT | CGTGCCCAGG | 840 |
| CAGAGCTCAA | TGCCTTGAAA | CGAACAGAAG | AAGACCTGAA | AAAGGGTCAC | AGAAACTGG | 900 |
| AAGAGATGGT | TACCCGTTTA | GATCAAGAAG | TAGCCGAGGT | TGATAAAAAC | ATAGAACTTT | 960 |
| TGAAAAAGAA | GGATGAAGAA | CTCAGTTCTG | CTCTGGAAAA | AATGGAAAAT | CAGTCTGAAA | 1020 |
| ACAATGATAT | CGATGAAGTT | ATCATTCCCA | CAGCTCCCTT | ATACAAACAG | ATCCTGAATC | 1080 |
| TGTATGCAGA | AGAAAACGCT | ATTGAAGACA | CTATCTTTTA | CTTGGGAGAA | GCCTTGAGAA | 1140 |
| GGGGCGTGAT | AGACCTGGAT | GTCTTCCTGA | AGCATGTACG | TCTTCTGTCC | CGTAAACAGT | 1200 |
| TCCAGCTGAG | GGCACTAATG | CAAAAAGCAA | GAAAGACTGC | CGGTCTCAGT | GACCTCTACT | 1260 |

```
GACTTCTCTG ATACCAGCTG GAGGTTGAGC TCTTCTTAAA GTATTCTTCT CTTCCTTTTA    1320

TCAGTAGGTG CCCAGAATAA GTTATTGCAG TTTATCATTC AAGTGTAAAA TATTTTGAAT    1380

CAATAATATA TTTTCTGTTT TCTTTTGGTA AAGACTGGCT TTTATTAATG CACTTTCTAT    1440

CCTCTGTAAA CTTTTGTGC TGAATGTTGG GACTGCTAAA TAAAATTTGT TTTT           1494
```

( 2 ) INFORMATION FOR SEQ ID NO:4:

( i ) SEQUENCE CHARACTERISTICS:
        ( A ) LENGTH: 380 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Val Ser Lys Tyr Lys Tyr Arg Asp Leu Thr Val Arg Glu Thr Val
 1               5                  10                  15
Asn Val Ile Thr Leu Tyr Lys Asp Leu Lys Pro Val Leu Asp Ser Tyr
             20                  25                  30
Val Phe Asn Asp Gly Ser Ser Arg Glu Leu Met Asn Leu Thr Gly Thr
         35                  40                  45
Ile Pro Val Pro Tyr Arg Gly Asn Thr Tyr Asn Ile Pro Ile Cys Leu
     50                  55                  60
Trp Leu Leu Asp Thr Tyr Pro Tyr Asn Pro Pro Ile Cys Phe Val Lys
 65              70                  75                  80
Pro Thr Ser Ser Met Thr Ile Lys Thr Gly Lys His Val Asp Ala Asn
                 85                  90                  95
Gly Lys Ile Tyr Leu Pro Tyr Leu His Glu Trp Lys His Pro Gln Ser
            100                 105                 110
Asp Leu Leu Gly Leu Ile Gln Val Met Ile Val Val Phe Gly Asp Glu
        115                 120                 125
Pro Pro Val Phe Ser Arg Pro Ile Ser Ala Ser Tyr Pro Pro Tyr Gln
    130                 135                 140
Ala Thr Gly Pro Pro Asn Thr Ser Tyr Met Pro Gly Met Pro Gly Gly
145                 150                 155                 160
Ile Ser Pro Tyr Pro Ser Gly Tyr Pro Pro Asn Pro Ser Gly Tyr Pro
                165                 170                 175
Gly Cys Pro Tyr Pro Pro Gly Gly Pro Tyr Pro Ala Thr Thr Ser Ser
            180                 185                 190
Gln Tyr Pro Ser Gln Pro Pro Val Thr Thr Val Gly Pro Ser Arg Asp
        195                 200                 205
Gly Thr Ile Ser Glu Asp Thr Ile Arg Ala Ser Leu Ile Ser Ala Val
    210                 215                 220
Ser Asp Lys Leu Arg Trp Arg Met Lys Glu Glu Met Asp Arg Ala Gln
225                 230                 235                 240
Ala Glu Leu Asn Ala Leu Lys Arg Thr Glu Glu Asp Leu Lys Lys Gly
                245                 250                 255
His Gln Lys Leu Glu Glu Met Val Thr Arg Leu Asp Gln Glu Val Ala
            260                 265                 270
Glu Val Asp Lys Asn Ile Glu Leu Lys Lys Lys Asp Glu Glu Leu
        275                 280                 285
Ser Ser Ala Leu Glu Lys Met Glu Asn Gln Ser Glu Asn Asn Asp Ile
    290                 295                 300
Asp Glu Val Ile Ile Pro Thr Ala Pro Leu Tyr Lys Gln Ile Leu Asn
305                 310                 315                 320
```

```
Leu Tyr Ala Glu Glu Asn Ala Ile Glu Asp Thr Ile Phe Tyr Leu Gly
            325             330                 335

Glu Ala Leu Arg Arg Gly Val Ile Asp Leu Asp Val Phe Leu Lys His
            340             345                 350

Val Arg Leu Leu Ser Arg Lys Gln Phe Gln Leu Arg Ala Leu Met Gln
            355             360             365

Lys Ala Arg Lys Thr Ala Gly Leu Ser Asp Leu Tyr
370             375                 380
```

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
His Thr His Leu Ala Met Asx Asp Ala
1               5
```

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Phe Xaa Asn Gly Ala Leu Glx Cys Tyr Ser
1               5                   10
```

METHOD FOR CONCURRENT DISRUPTION OF EXPRESSION OF MULTIPLE ALLELES OF MAMMALIAN GENES

ACKNOWLEDGEMENTS

This invention was supported in part by grant NIH HG 00325. The U.S. Government may have rights in this invention.

This application claims the benefit of U.S. Provisional application Ser. No. 60/006856, filed Nov. 16, 1995.

INTRODUCTION

1. Technical Field

The field of the subject invention is a method for identifying and isolating, in the absence of knowledge of the sequence of, genes whose homozygous functional knock out is required to produce a defined phenotype.

2. Background

Methods for identifying genes in a mammalian cell by inactivating the gene typically suffer from several drawbacks. First of all, mammalian cells commonly deployed are diploid for most genes, and the identification of cells containing lesions that produce recessive phenotypes requires that multiple alleles of the gene be inactivated. Normally, the inactivation step results in inactivation of only a single gene copy. The other gene copy may still be expressed, and the phenotype of the cell containing the inactivated gene may be indistinguishable from the wild-type phenotype. While homozygous inactivation of previously cloned genes has been accomplished by gene targeting and homologous recombination combined with appropriate selection techniques, this cannot be done unless the gene has been cloned previously or its sequence known. Similarly, homozygous inactivation of multiple alleles of genes can be accomplished using antisense RNA or antisense nucleotides, but again, this requires prior cloning of the gene and/or knowledge of its sequence.

It is often tedious to confirm that a specific lesion is associated with the change in cell phenotype. The chromosomal locus containing the lesion is identified, and a putative gene sequence obtained. The gene sequence is cloned into an appropriate vector which will allow for stable expression of a normal gene sequence in the mammalian cell. The vector is then introduced into a cell containing homozygously inactivated copies of the gene for complementation of the initial lesion to obtain the wild-type phenotype. In many cases, unfortunately, no complementation is observed.

Therefore, there is considerable interest in developing a method for identifying mammalian cell genes whose concurrent homozygous inactivation de novo leads to a defined phenotype, where multiple alleles of a gene have been inactivated and where it is easy to confirm that the inactivation of the alleles has resulted in a cell phenotype distinguishable from the wild-type phenotype.

Relevant Literature

Baubonis and Sauer, *Nucl. Acid Res.* (1993) 9:2025–2029 describe precise excision of genomic DNA flanked by directly repeated lox sites by cre recombinase. Craig, *Ann. Rev. Genet.* (1988) 22:77–105 reviews the mechanism of conservative site-specific recombination.

Baim et al., *Proc. Natl. Acad. Sci. USA* (1991) 88:5072–5076 describes a chimeric mammalian transactivator based on the lac repressor that is regulated by temperature and isopropyl beta-D-thiolactopyranoside.

Lemke et al., *Glia* (1993) 7:263–271 describes loss of function mutations engineered through the expression of antisense RNA from previously cloned genes and through the insertional inactivation of the $P_0$ gene, by homologous recombination in embryonic stem cells, and the generation of $P_0$-deficient mice.

Kamano et al. Leukemia Res. (1990) 10:831–839, van der Krol et al., *Biotechniques* (1988) 6:958, Katsuki et al., *Science* (1988) 241:593–595 Owens et al,. *Development* (1991) 112:639–649, and Owens et al., *Neuron* (1991) 7:565–575 describe changes in cell phenotype associated with the expression of antisense RNAs in different cell types.

Giese et al., *Cell* (1992) 71:565–576 describes the inactivation of both copies of a gene in a transgenic mouse.

SUMMARY OF THE INVENTION

The subject invention, in one aspect, provides a method for identifying de novo a gene at a random chromosomal locus of a mammalian cell based on the phenotype produced by interfering with expression of multiple alleles of the gene corresponding to this locus. The method involves inactivating all copies of the gene and any of its alleles which have substantial sequence similarity.

One copy of the gene is inactivated by the integration of a DNA construct at a random or unselected chromosomal locus, or one that is selected for its proximity to an expressed gene. The construct integrated at the random chromosomal locus contains a transcription initiation region sequence responsive to a transactivation factor. Transcription occurs in the opposite direction to a coding region for a promoterless positive selection marker gene. Hereinafter, the transactivation factor responsive transcriptional initiation region will be referred to as the "TF promoter." The positive selection marker gene carried by the construct is expressed only when the construct is integrated 3' in relation to an endogenous gene promoter, with the endogenous promoter directing transcription toward the positive selection marker gene. Expression of the positive selection marker gene may also require that it be in the correct reading frame to express an active positive selection marker, either fused or non-fused to the expression product of a portion of the endogenous gene at the locus of integration.

Additionally, either the TF promoter is activated by a factor which can be added to the medium or by a transactivation factor encoded and expressed by a second construct, which second construct is introduced into the host. This factor serves to activate antisense RNA transcription from the TF promoter. Antisense RNA transcription from the TF promoter extends in the 3' direction relative to the orientation of the TF promoter, and into the flanking chromosomal locus 5' to the insertion of the marker gene. Binding or hybridization of the antisense RNA transcription product initiated from the TF promoter inhibits expression of the other alleles which have substantially similar sequence to the chromosomal DNA sequence transcribed from the TF promoter, and sequences complementary to the antisense RNA. (By "similar sequence" is intended sufficient similarity to bind to a messenger RNA sequence to provide an observable change in the function of the messenger RNA sequence). In this way, the production of all of the same or allelic proteins, including enzyme isoforms, may be prevented.

By first introducing the construct with the promoterless marker gene, one can select for cells in which the marker gene is being expressed, so that there is a high likelihood that the construct is positioned in an actively transcribed gene. By expanding these cells, one may then use these cells for introduction of the expression construct containing the transactivation factor gene. This expression construct will have its own marker gene, so that one can select for those cells which have the transactivation factor expression construct. The resulting cells should, for the most part, be cells which transcribe a transcription product antisense to the construct encoded by the gene containing the inserted construct, which results in inhibition of expression of proteins by all alleles of the locus at which the promoterless marker gene integrated.

The cells which have been selected for the markers associated with the two constructs may now be screened to determine whether gene inactivation has resulted in a specifically desired cell phenotype distinguishable from the wild-type phenotype, or alternatively selection of cells expressing the desired phenotype can be carried out. Additionally, the chromosomal locus flanking the 5' end of the integrated construct may be identified.

As a further check on whether the observed change in phenotype is as a result of the transcription of an antisense strand, the transcription of the antisense strand can be reversed by introducing a third construct into cells with a modified phenotype. This construct comprises an expression construct expressing a recombinase gene sequence that would serve to excise the transactivation gene or the TF promoter, where flanking consensus sequences recognized by the recombinase gene are present in the transactivation and/or TF promoter constructs, resulting in the excision of these elements, and such other portions of the construct as are deemed appropriate. Alternatively, turn off of the antisense promoter can be accomplished by using a promoter that is regulated by hormones, chemical agents, temperature, or other agents.

In another aspect, the subject invention provides a rapid method for establishing the function of a gene in a mammalian cell of which at least a portion of the sequence has been previously isolated. In this aspect, the construct integrated in the genome includes two homologous recombination sites which allow for the integration of the construct at the target site. Additionally, the subject invention provides for DNA constructs, vectors, and mammalian cells containing the DNA constructs in their genome.

BRIEF DESCRIPTION OF THE SEQUENCES

Sequence ID Nos. 1 and 2 are sequences of mouse tsg101 cDNA and predicted amino acid sequence of the Tsg101 protein. The site of translation initiation is underlined. The splice junction 5' to β-geo is boxed and the poly(A) signal is shown in bold type. The predicted coiled-coil domain is shaded.

Sequence ID Nos. 3 and 4 are sequences of human tsg101 cDNA and predicted amino acid sequence of the Tsg101 protein. The site of translation initiation is underlined. The splice junction 5' to β-geo is boxed and the poly(A) signal is shown in bold type. The predicted coiled-coil domain is shaded.

DESCRIPTION OF THE SPECIFIC EMBODIMENTS

The subject invention provides a method for identifying a gene at a random chromosomal locus of a mammalian cell on the basis of a phenotype produced by homozygous inactivation of gene function. The method includes the concurrent inactivation of other copies of the genes or alleles of the gene, which are substantially similar in their DNA sequence, followed by a determination of whether inactivation of the gene and its alleles has resulted in a cell phenotype distinguishable from the wild-type phenotype. Additionally, the chromosomal locus containing the inactivated gene may be identified.

The method includes the preparation and introduction of a gene search construct that includes a TF promoter and a construct that expresses a transactivator protein, normally the introduction being sequential, into a mammalian cell. (By "gene search construct" is intended a promoterless reporter gene and 5' sequences that may generate fusion transcripts originating in DNA 5' to the reporter gene, so that the fusion construct will include any portion of the coding region of the endogenous gene between the endogenous promoter and the 5' sequence of the construct, the 5' sequence of the construct and also all or functional part of the reporter gene. By "transactivator construct" is intended a DNA molecule which comprises a transcriptional initiation region, a translational initiation sequence, a coding sequence encoding a protein that activates the TF promoter, and a translational and transcriptional termination region. All of the regions and sequences will be functional in the host of interest). Preferably, a first construct ("gene search construct") comprising a promoterless marker gene and a transactivation factor responsive promoter ("TF promoter"), directing transcription in the opposite direction of the coding region of the promoterless marker gene, is introduced first into the cells and the cells expanded and selected for cells which express the promoterless marker gene. At this time, the TF promoter is inactive and will not interfere with the transcription of the promoterless marker gene, A second construct may also be introduced which expresses a marker gene and a transactivation factor which acts on the TF promoter to activate the promoter, resulting in transcription of an antisense strand. As transcription of the antisense strand extends into the chromosomal DNA flanking the gene search construct, it serves to inactivate other genes having substantially similar sequences to the antisense strand of flanking DNA. Those cells having the gene search construct, with the first construct at a locus which provides for expression of the promoterless marker gene, will under conditions of transactivation be screened or selected for change in phenotype.

Rather than activate the TF promoter with a transactivation factor from expression of the expression construct, one may employ a TF promoter which is responsive to agents, e.g., compounds or other stimuli, which may be added to the medium or provided as a change in environment, e.g. heat. There are many promoters which have responsive elements, e.g., tetracycline or hormonal, such as steroid, responsive elements, where compounds can be added to the medium which will turn on the TF promoter, e.g., tetracycline derivatives or hormones, such as glucocorticoids.

To further establish whether the change in phenotype is as a result of the production of an antisense sequence, one may provide for reversal of the transcription of the antisense sequence, by providing at least one of the constructs with sequences that result in excision of the DNA region between the excision sequences. One introduces a third construct, a recombinase expression construct, into the host comprising a marker gene and a gene encoding a recombinase which acts on the excision sequences for excision. The cells may then be screened for reversal of the phenotype, indicating that the phenotype was the result of the production of the antisense sequence. Alternatively, expression of the antisense promoter or of a transactivator protein that turns on this promoter can be regulated using one or more of the agents indicated above and below.

The transcriptional initiation region of the TF promoter or of the transactivator gene employed in this invention may be varied widely, as by the particular application. The transcriptional initiation region of the TF promoter or transactivator gene may be constitutive or inducible, as appropriate, may include enhancers, repressors, or other regulatory sequences, which may be regulated in cis or trans. Regulation may also be as a result of additives to the media, e.g., tetracycline or hormones, e.g., glucocorticoids. The initiation region may be from any source, where the initiation region is functional in the host. Thus, the initiation region may be from structural genes of the host, from viral genes functional in the host, or combinations of such promoter regions, or synthetic promoter regions, as appropriate. The promoter region may be a single promoter region (associated with a single gene) or a combination of 5' regions associated with different genes. The promoter region will usually be chosen to provide the desired level of transcription for the particular coding region or gene. Promoters which may find use in mammalian cells include SV40 promoters, glucocorticoid inducible promoters, CMV promoters, β-actin promoters, etc. The coding region or gene will be under the transcriptional and translational regulation of the initiation region. There will also be a translational and transcriptional termination region downstream in the direction of transcription from the gene. Since, for the most part, the termination region is not important to the functioning of expression, a wide variety of termination regions may be used from a wide variety of host genes, viral genes functional in the host, or the like.

For producing the antisense RNA, a promoter is employed which will not be active in the cell, except in conjunction with a transactivation factor or other inducing agent or condition necessary to activate the promoter. (See the above discussion concerning inducible promoters). This factor will be necessary for transcription initiation and can be supplied by a second construct introduced into the host cell or by adding the appropriate agent or providing the appropriate condition(s) for activation of the TF promoter. With the expression construct which will not be required if induction of transcription does not require a transactivator protein, one can ensure strong binding of the transactivation factor to the TF promoter, desirably using a chimeric protein which combines a DNA-binding domain and a transcription factor, which directly or indirectly binds to RNA Polymerase II. The DNA-binding domain binds to a DNA sequence which desirably is not found in mammalian cells, and therefore would not be expected to bind at endogenous mammalian promoters. The DNA-binding domain allows for potent binding of the transactivation factor to a unique DNA sequence while orienting the transcription factor close to an RNA polymerase II binding site for interaction of the transcription factor with the transcriptional machinery of the host mammalian cell.

The marker gene of the expression construct expressing the transactivator may be a single gene or a fused gene comprising two different markers which may be selected differentially. Single gene markers include neo, which can provide for G418 resistance. Combination genes may include lacZ and aminoglycoside phosphotransferase (aph) which provides G418 resistance, hygromycin resistance (hyg) and the herpes simplex thymidine kinase (TK) gene, which provides resistance to hygromycin and sensitivity to ganciclovir.

The DNA-binding domain of the transactivator protein will usually be from a host foreign to the target host, usually a unicellular microorganism, insect, plant or the like, so as to be unlikely to be recognized by DNA binding proteins in the host, while the transcriptional activation domains will be from the host or other source which provides a factor which binds to the target host RNA polymerase II. Conveniently, the DNA-binding domain is derived from a DNA-binding protein isolated from bacterial cells and the transcription activation domain is derived from a transcription activation domain that binds to RNA polymerase II from a common genus, e.g., mammalian cells for a mammalian host.

In a preferred embodiment, the transactivation factor contains the DNA-binding domain of the lac repressor at its amino terminus and the transcription activation domain from the herpes simplex virus virion protein 16 (VP16) at its carboxyl terminus, or the like.

The first DNA construct comprising the promoterless marker gene may also be referred to as the "knockout" construct. This knockout construct includes the TF promoter which comprises the DNA sequence bound by the transactivation factor. The expression construct comprising the transactivation factor gene or second construct could be part of the first construct or be introduced first, but this would not allow cells to be selected for appropriate integration at a gene locus and then subsequent expansion, without the complication of the antisense RNA also being produced, which might interfere with expression of the marker. It is therefore desirable that the second construct be introduced after cells having integration of the first construct downstream from a promoter have been selected, unless the transactivation factor gene is inducible, so that transcription of the transactivation gene may be initiated after selection for integration of the knockout construct.

The TF promoter typically includes a region consisting of sequence repeats, two or more, usually at least about 5 and not more than 20, and in a preferred embodiment, 14, which are tightly bound by the DNA-binding domain of the transactivation factor. Additionally, the TF promoter includes a promoter sequence for binding the RNA polymerase II of the host cell to place RNA polymerase II in close relationship with the transcription initiation domain. In a preferred embodiment the promoter sequence responsive to the transactivation factor consists of a minimal SV-40 promoter, which lacks the enhancer sequences and GC-rich sequences typically found in the SV-40 early transcription promoter, but which can still bind the RNA polymerase, and spaced sets of lac operators located upstream from the promoter.

The lac operator sequences cause strong binding of the lac repressor DNA-binding domain at the transcription initiation region. The minimal SV-40 promoter binds the RNA polymerase II, which is also bound by the transcription factor of the chimeric protein to enhance transcription from the TF promoter.

The transcription initiation region is oriented so that RNA transcription initiated from the transcription initiation region extends into the chromosomal locus flanking the knockout construct at its 5' end to provide for the antisense transcript on the non-coding strand, so as to be complementary to the sense strand from which the mRNA is transcribed.

The knockout construct also includes a coding region sequence for a positive selection marker. The term "coding region sequence" ordinarily refers to the coding region for a polypeptide without a promoter. The coding region sequence is located so as to allow for fusion of the coding region sequence with an exon of the gene into which the gene search construct is integrated, usually upstream (5' direction) in relationship to the direction of transcription of the TF promoter. The coding region sequence is conveniently downstream of the TF promoter, where a splice site may be employed which is positioned to remove the TF promoter when the coding region sequence is spliced to a chromosomal exon. Since the positive selection marker coding region sequence lacks a promoter and the transactivatable antisense promoter region sequence is oriented in the opposite direction, the selection marker coding region sequence is only expressed if the knockout construct is integrated downstream from an endogenous gene promoter. Additionally, when integrated within a translated portion of the gene, the coding region needs to be in the correct reading frame to form a fused protein consisting of an active positive selection marker and the truncated polypeptide of the gene. This can be done by including 5' to the positive selection marker a splice acceptor sequence in one or more translational reading frames.

Optionally, the knockout construct contains a splice acceptor sequence which is located usually about 20 or fewer base pairs upstream of the positive selection marker region, although it may be within or downstream from the TF promoter. The splice acceptor sequence is useful in case the knockout construct has integrated at an intron or 3' UTR of a chromosomal gene and is employed for splicing the precursor RNA to incorporate the positive selection marker gene sequence in the mRNA. If the coding sequence is incorporated into the 5' UTR, the coding sequence will include an initiation codon.

The knockout construct with the 3'-splice site may be organized with the TF promoter upstream or downstream from the 3'-splice site (if downstream, desirably the TF promoter sequence will lack a stop codon in phase with the coding region sequence); the 3'-splice site; and the coding region sequence.

To obtain integration one may introduce the bare DNA into the host cell. Preferably a construct will be used which enhances integration, such as an integrating virus, e.g., self-inactivating Moloney Murine Leukemia Virus, adenovirus, transposons and a transposase, etc. Alternatively integrating of DNA can be accomplished following introduction of naked DNA by electroporation. Depending upon the particular vector employed for integration, the integration may be more or less random, depending on whether the vector has sequence preferences. It should be noted that retroviral insertions have some preference for actively transcribed regions, so that there will be some enrichment for integration into genes with retroviral integration sequences.

Stable maintenance of the first and second constructs in the mammalian cell and integration of the knockout construct at a random chromosomal locus as described above, where the promoterless marker gene is placed under the transcriptional construct of an endogenous promoter, results in (i) expression of the positive selection marker coding region sequence, and (ii) in conjunction with transactivation factor expression or availability, binding of the factor to the transcription initiation region sequence activating antisense RNA transcription extending into the 5' region of the gene locus in relation to the TF promoter.

One copy of the gene is inactivated by the insertion of the knockout construct in its sequence. Expression of other copies of genes similar, particularly complementary, to the antisense transcript is inhibited. The antisense RNA forms duplexes with cellular RNAs that are similar to the antisense RNA transcript. Duplex formation inhibits the function of such cellular RNAs. Such inactivation of the related genes may cause a change in the phenotype of the cells.

In order to investigate whether a change in phenotype is associated with the antisense RNA production, one provides for reversal of the production of the RNA antisense. Optionally, the first and/or second constructs may contain two site-specific specific recombination sites delimiting the regions associated with the production of the antisense sequence. That is, they may delimit the TF promoter and/or the transactivation gene sequence. Preferably, these sites delimit the transactivation gene sequence or functional portion thereof, e.g., promoter or coding region. In order to provide for excision of the sequence(s) associated with the production of the antisense RNA, a third DNA construct (recombinase expression construct) containing a recombinase gene may be prepared and integrated into the host comprising the first and second constructs. A marker gene may also be provided as part of the construct, so as to select for cells into which the recombinase construct has integrated. These selected cells may be expanded and screened for change of phenotype. Alternatively, where the transactivation factor is provided extrinsic to the cells, the medium or environment may be changed to stop transcription of the antisense sequence. Another alternative is to regulate the antisense (TF) promoter by use of hormones, Tc, etc.

If regulation by removal of the transactivator is desired, the sequence between the consensus sequences for deletion comprises a negative selection marker, particularly in conjunction with the gene expressing the transactivation factor. Expression of the recombinase gene typically causes the excision of a fragment of the transactivation factor construct's DNA which contains the gene for the transactivation factor and the gene for the negative selection marker. The cells may then be selected for lack of expression of the negative selection marker.

The recombinase is an enzyme which causes the excision of any DNA sequence that is delimited by site-specific recombination sites. These site-specific recombination sites are sequences typically between 20 to 100 base pairs, usually about 30 to 50 base pairs and are exogenous to the host cell. Site-specific recombination sites contain two recombinase recognition sequences in inverted orientation at an overlap region. The recombination sites are oriented as repeats to cause segment excision. The recombinase may be a member of the integrase protein family which includes cre protein, int protein and FLP protein.

Expression of the recombinase in a mammalian cell causes excision of the DNA fragment which is delimited by the two site-specific recombination sites and which will desirably include the transactivation factor coding region sequence. The transactivation factor is therefore no longer expressed, and antisense RNA transcription is no longer initiated from the knockout construct. Typically, the cell phenotype, where there are two or more copies of the gene, should revert to the wild-type phenotype, where the previous change in phenotype was as a result of the production of the antisense sequence.

All the DNA constructs contain selection marker gene sequences for monitoring insertion of the constructs in mammalian cells comprising the different construct genes and for allowing for selection of such cells substantially free of other cells not comprising the construct sequences. The positive selection marker gene is a gene sequence that allows for selection of target cells in which the subject constructs have been introduced. Positive selection marker genes include the neo gene for resistance to G418, the hygromycin resistance gene, and the like. A negative selection marker gene is typically the herpes simplex virus thymidine kinase (tk) gene, whose expression can be detected by the use of nucleoside analogs, such as acyclovir or gancyclovir, for their cytotoxic effects on cells that contain a functional tk gene.

As discussed above, the knockout construct contains a coding region sequence for a positive selection marker to select for cells expressing the positive selection marker. The positive selection marker is only expressed if it is downstream in relationship to an endogenous promoter and, when fused to a coding region, is fused in frame with the native protein.

The transactivation factor construct contains a positive selection marker gene to select for cells expressing the positive selection marker. The transactivation construct may also include a negative selection marker gene in the DNA fragment that is excised from the construct in the presence of a recombinase. In this manner the excision of the DNA fragment containing the transactivation factor gene sequence is monitored.

Additionally, the constructs may contain other sequences required for manipulation of the constructs. For example, restriction sites are necessary for manipulating the sequences in the constructs. Other sequences which may be present include primer initiation sequences for amplifying DNA, origins for cloning, markers for cloning hosts, sequences aiding in integration into the host chromosome, and the like.

The constructs may be included in vectors for introducing the constructs into mammalian cells. When the vectors are introduced into a cell by retroviral infection, these sequences include long terminal repeats and packaging signals. When the introduced vectors are to replicate episomally in a mammalian cell, the vectors include a viral origin of replication.

According to the subject invention, both knockout and transactivator constructs ordinarily are introduced into the target mammalian cells. Particularly the mammalian cells are mouse cells, rat cells, primate cells, e.g., sequentially human cells, rabbit cells or the like. Other eukaryotic hosts may also be used, such as plant cells, insect cells, fish cells, fungal cells, and the like. The mammalian cells may be normal cells, in a differentiated or undifferentiated state, e.g., stem cells. Alternatively, the cells may be transfected with naked DNA. Desirably, the cells are maintainable in culture and allow for the introduction of new genetic material.

The constructs may be introduced into the target cell in accordance with known ways. For example, the constructs may be introduced by retroviral infection, electroporation, fusion, polybrene, lipofection, calcium phosphate precipitated DNA, or other conventional techniques. Particularly, the knockout construct is introduced by viral infection for largely random integration of the construct in the genome. The transactivation construct is introduced into cells by any of the methods described above. After introduction of each construct into target mammalian cells, the cells are grown in a selective medium to select for cells that express the appropriate selection markers, substantially free of cells that do not express the selection markers. For example, cells receiving a knockout construct containing the neomycin coding region sequence are grown in a medium containing G418, and cells receiving a transactivation construct containing the hygromycin resistance gene sequence are grown in a medium containing hygromycin.

Stable expression of the first positive selection marker coding sequence indicates that the knockout construct has been integrated into a chromosomal locus, downstream of an endogenous promoter. Stable expression of the second positive selection marker gene sequence indicates that the transactivation construct has been stably introduced in the cells.

The cells that have received the knockout construct and stably express both positive selection markers are assayed for a cell phenotype distinguishable from the wild-type phenotype. Different types of phenotypes may include changes in growth pattern and requirements, sensitivity or resistance to infectious agents or chemical substances, changes in the ability to differentiate or nature of the differentiation, changes in morphology, changes in response to changes in the environment, e.g., physical changes or chemical changes, changes in response to genetic modifications, and the like.

For example, the change in cell phenotype may be the change from normal cell growth to uncontrolled cell growth. The cells may be screened by any convenient assay which provides for detection of uncontrolled cell growth. One assay which may be used is a methylcellulose assay with bromodeoxyuridine (BrdU). Another assay which is effective is the use of growth in agar (0.3 to 0.5%>thickening agent). A test for tumorigenicity may also be used, where the cells may be introduced into a susceptible host, e.g., immunosuppressed, and the formation of tumors determined.

Alternatively, the change in cell phenotype may be the change from a normal metabolic state to an abnormal metabolic state. In this case, cells are assayed for their metabolite requirement, such as amino acids, sugars, cofactors, or the like, for growth. Initially, about 10 different metabolites may be screened at a time to assay for utilization of the different metabolites. Once a group of metabolites has been identified that allows for cell growth, where in the absence of such metabolites the cells do not grow, the metabolites are screened individually to identify which metabolite is assimilable or essential.

Alternatively, the change in cell phenotype may be a change in the structure of the cell. In such a case, cells might be visually inspected under a light or electron microscope.

The change in cell phenotype may be a change in the differentiation program of a cell. For example, the differentiation of myoblasts to adult muscle fibers can be investigated. The differentiation of myoblasts can be induced by an appropriate change in the growth medium and can be monitored by determining the expression of specific polypeptides, such as myosin and troponin, which are expressed at high levels in adult muscle fibers.

The change in cell phenotype may be a change in the commitment of a cell to a specific differentiation program. For example, cells derived from the neural crest, if exposed to glucocorticoids, commit to becoming adrenal chromaffin cells. However, if the cells are exposed instead to fibroblast growth factor or nerve growth factor, the cells eventually become sympathetic adrenergic neuronal cells. If the adrenergic neuronal cells are further exposed to ciliary neurotrophic factor or to leukemia inhibitory factor, the cells become cholinergic neuronal cells. Cells transfected by the method of the subject invention can therefore be exposed to either glucocorticoids or any of the factors, and changes in the commitment of the cells to the different differentiation pathways can be monitored by assaying for the expression of polypeptides associated with the various cell types.

After establishing a change in phenotype, the chromosomal region flanking the knockout construct DNA may be identified using PCR with the construct sequence as a primer for unidirectional PCR, or in conjunction with a degenerate primer, for bidirectional PCR. The sequence may then be used to probe a cDNA or chromosomal library for the locus, so that the region may be isolated and sequenced. Alternatively, the region knocked out by antisense RNA may be sequenced and, if a large enough portion is identified, the coding region may be used in the sense direction and a polypeptide sequence obtained. The resulting peptide may then be used for the production of antibodies to isolate the particular protein. Also, the peptide may be sequenced and the peptide sequence compared with known peptide sequences to determine any homologies with other known polypeptides. Various techniques may be used for identification of the gene at the locus and the protein expressed by the gene, since the subject methodology provides for a marker at the locus, obtaining a sequence which can be used as a probe and, in some instances, for expression of a protein fragment for production of antibodies. If desired the protein may be prepared and purified for further characterization.

The subject method, in another aspect, is employed to identify the function of a gene when at least part of the sequence of the gene is known. The method includes the inactivation of both gene copies to determine a change in cell phenotype, or a loss of function, associated with the inactivation of specific alleles of the gene.

The method includes the preparation of a knockout construct including both the promoter region sequence and the positive selection marker coding region sequence. Additionally, the construct contains two homologous recombination sites delimiting the promoter region sequence and the positive selection marker sequence. These homologous recombination sites are homologous to sequences of the known gene and allow for insertion of the knockout construct sequence flanked by the two recombination sites into the known gene.

These homologous recombination sites will typically be not more that about 2 kbp, usually not more than 1 kbp. The sites will typically be not less than 0.05 kbp, usually not less that 0.1 kbp. The regions of homology between these recombination site sequences and the target sequences will typically be at least about 90%, usually greater than 95%. The regions of homology are preferably within coding regions, such as exons, of the gene.

Additionally, the knockout construct may contain the transactivation factor gene sequence, so that no other construct is required for performing the subject invention.

Using this approach, one may inhibit expression of the alleles of a gene, where only a partial sequence is known and determine whether the expression product has an effect on phenotype, since all of the copies of the gene and related alleles may be inhibited from expression. In this manner, without knowing what the gene is, one may conveniently determine whether the function of the gene is of interest.

Exemplifying the power of the subject technology is the identification of the gene tsg101. Amino acids 231 to 301 of tsg101 are identical, except for 2 mismatches to cc2, an α-helix domain encoded by partial cDNA clone identified by its ability to express a protein that interacts with stathmin (Maucuer et al. (1995) *PNAS USA* 92, 3100-3104), an evolutionarily-conserved phosphoprotein implicated in the integration and relay of diverse signals regulating cell growth. Other structural features of the protein are described in the experimental section. The gene is obtained as a chromosomal fragment, where it is less than about 100 kbp, usually less than about 50 kbp, or as cDNA. The tsg101 coding sequence will usually be flanked by nucleic acid sequences other than the sequences present at its natural chromosomal locus, where the different sequence will be within 10 kbp of the tsg101 coding sequence. The protein may be obtained in purified form freed of other proteins and cellular debris, generally being at least about 50 weight % of total protein, more usually at least about 75 weight % of total protein, more usually at least about 95 weight % of total protein, and up to 100%. Similarly the nucleic acid encoding sequences, including fragments of at least 18 bp, more usually at least 30 bp, generally including a fragment encoding a functional domain, e.g., coiled-coil, α-helix, leucine zipper, etc., will be obtained in analogous purity, except that the percentages are based on total nucleic acids, comparing nucleic acid molecules having tsg101 coding sequences to nucleic acid molecules lacking such sequences.

The inhibition of tsg101 expression results in a neoplastic phenotype. Therefore, the gene may be used in a variety of ways. The gene can be used for the expression and production of Tsg101 to identify agents which inhibit Tsg101 to determine the role that Tsg101 plays in the neoplastic phenotype. Since under- and overproduction of Tsg101 induces colony formation on 0.5% agarose, by modulating the level of Tsg101 in cells in conjunction with other agents, one can elucidate the pathway to neoplasia associated with Tsg101. Tsg101 may be used to produce antibodies, antisera or monoclonal antibodies, for assaying for the presence of Tsg101 in cells. The DNA sequences may be used to determine the level of mRNA in cells to determine the level of transcription. In addition, the gene may be used to isolate the 5' non-coding region to obtain the transcriptional regulatory sequences associated with tsg101. By providing for an expression construct which includes a marker gene under the transcriptional control of the tsg101 transcriptional initiation region, one can follow the circumstances under which tsg101 is turned on and off. Also, the gene may be used in gene therapy and knockout animal models to identify the role of Tsg101 in development of a fetus.

Tsg101 can be used to investigate the interactions with strathmin and the role the complex plays in the regulation of the cell.

Because of the high conservation of tsg101, fragments of the gene may be used to identify other genes having homologous sequences using low stringency hybridization and the same and analogous genes from other species, such as primate, particularly human, and the like.

The tsg101 gene or fragments thereof may be introduced into an expression cassette for expression or production of antisense sequences the expression cassette will include upstream and downstream in the direction of transcription, a transcriptional and translational initiation region, the tsg101 gene, followed by the translational and transcriptional termination region, where the regions will be functional in the expression host cells. The transcriptional region may be native or foreign to the tsg101 gene, depending on the purpose of the expression cassette and the expression host. The expression cassette may be part of a vector, which may include sites for integration into a genome, e.g., LTRs, homologous sequences to host genomic DNA, etc., an origin for extrachromosomal maintenance, or other functional sequences.

The following examples are offered by way of illustration and not by way of limitation.

EXPERIMENTAL

The method described below allows for the identification and isolation of new genes involved in the regulation of cell growth and differentiation. Preparation of constructs, methods for mammalian cell transformation, assays for uncontrolled cell growth, and methods for identifying the new gene are provided.

Results

Experimental Approach and Construction of Gene Search Vectors pLLGSV, a retroviral gene search vector derived from self-inactivating Moloney murine leukemia virus (MLV) (Hawley et al., *PNAS USA* (1987) 84:2406–2410; Brenner et al., *PNAS USA* (1989) 86:5517–5521) carries the β-geo (Friedrich and Soriano, *Genes & Develop.* (1991) 5:1513–1523) reporter gene. This reporter—a fusion of the *E. coli* lacZ and aminoglycoside phosphotransferase (aph or "neo") genes—encodes resistance to the antibiotic G-418, which was used to select and identify cells containing virus integrated into transcriptionally active chromosomal DNA regions behind chromosomal promoters. An adenovirus-derived splice acceptor (Friedrich and Soriano, 1991 supra) was inserted at the 5' end of β-geo to enhance the fusion of β-geo mRNA to upstream transcripts encoded by chromosomally-encoded exons. 5' to, and in reverse orientation to β-geo, is a regulated promoter formed by fusion of the SV40 early T antigen minimal promoter sequence to 14 *E. coli* lacZ operators (Labow et al., *Mol. Cell. Biol.* (1990) 10:3343–3356); this promoter has no transcription activity, but can be highly activated in trans by a transactivator, Lap348 (Labow et al., 1990, supra), containing the operator-binding domain of the *E. coli* lacI repressor and a the herpes simplex virus transactivation domain VP16. The system was designed to generate large amounts of antisense RNA, which interact not only with the sense RNA encoded by the allele with the integrated gene search vector, but also with the sense RNA encoded by other allele(s) of the same gene.

pLLGAV was first transfected into helper cells (GP+E-86) to generate infectious viruses to infect NIH3T3 cells. A population of G418 resistant NIH3T3 cells, containing the pLLGSV vector integrated at transcriptionally active sites behind chromosomal promoters throughout the 3T3 cell genome, were transfected with transactivator vector pLLTX. pLLTX encodes both the Lap348 and HyTK, a fusion of a hygromycin resistance (hyg) gene and the herpes simplex virus thymidine kinase (TK) gene (Lupton et al., *Mol. Cell. Biol.* (1991) 11:3374–3378). Transfectants expressing HyTK are resistant to hyg but sensitive to gancyclovir (gcv), which specifically kills cells expressing herpes TK. In contrast, in the absence of HyTK expression, cells are hyg-sensitive and gcv-resistant. Two lox sites from bacteriophage P1 flanking the transactivator and HyTK genes, allow excision of the Lap348/HyTK segment from chromosomes of cells by Cre, a lox-specific recombinase (Sauer and Henderson, *Nature* (1989) 298:447–451) expressed from pRSV-cre introduced into hyg resistant cells by electoporation. Cells in which the Lap348/HyTK segment has been excised, and in which the regulated promoter consequently has been turned off, are detected by their resistance to gcv.

hyg resistant NIH3T3 cells were plated in 0.5% agarose to select for transformation phenotype, i.e., to select genes whose inactivation may contribute to cellular transformation. Excision of LAP348 from transformed cells by Cre generated transactivator deleted clones. Comparing the phenotypes of the cells with transactivator present and cells with transactivator deleted, further confirms that cellular transformation results from transactivator generated antisense RNA. Cells with transactivator deleted can be used for cloning of the gene containing the gene search vector.

Isolation of Clones Showing Transformed Phenotype

$2.5 \times 10^8$ NIH 3T3 cells were infected with viral supernatant from a culture of a pLLGSV-transfected helper cell clone selected for its ability to produce a high titer of infectious virus. Infected cells containing chromosomally integrated pLLGSV were either selected on plates for G418 resistance or collected by fluorescence-activated cell sorting (Brenner et al., 1989, supra) for β-galactosidase activity; the cell population obtained by either method showed variable degrees of deep blue staining by X-gal. A pool of more than $5 \times 10^6$ clones containing retroviral integrations selected for G418 resistance was transfected with the transactivator vector pLLTX by electroporation; colonies selected for hyg resistance were pooled and plated in 0.5% agarose. Whereas no cells in a similarly-sized uninfected NIH 3T3 population formed colonies on this concentration of agarose, the pLLGSV infected population produced 20 colonies. One of these clones, SL6 was expanded into cell line, which was transfected with pRSV-cre to generate cells with deleted transactivator (SL6ΔT cells. Both SL6 and SL6ΔT cells were injected into nude mice subcutaneously, where only SL6 cells were highly tumorigenic. Although SL6ΔT cells produced a small tumor in one mouse, neither control NIH3T3 cells nor NIH3T3 cells transfected with pLLTX alone produced any tumor. Only SL6 cells produced spontaneous metastases to the lung. Replating of SL6, SL6ΔT and control cells into 0.5% agarose showed that only SL6 cells formed large colonies. To examine the regulation of reporter gene expression by transactivator, SL6 and SL6ΔT cells were assayed for β-galactosidase activity (Table 1). When transactivator was present in SL6 cells, expression of reporter gene was almost complete by shut off, compared to background control cells; when transactivator was removed by cre-lox recombination in SL6ΔT cells, the reporter gene was highly expressed. These results indicate that transactivator generated antisense RNA can effectively inactivate gene expression.

TABLE 1

Characterization of SL6

| Transactivator | 3T3 − | 3T3 + | SL6 − | SL6 + |
|---|---|---|---|---|
| β-Galactosidase Activity (U/μg) | 9.26[a] | 10.05 | 1225.80 | 19.88 |
| Growth in 0.5% Agarose | — | — | 20/10[5][b] | >1000/105 |
| Tumorigenicity in Nude Mice | 0/10 | 0/10 | 1/10 | 10/10 |
| Spontaneous Lung Metastasis[c] | 0/10 | 0/10 | 0/10 | 8/10 |

[a]Means of triplicates.
[b]The colonies formed by SL6 without transactivator were significantly smaller than those formed by SL6 with transactivator.
[c]Mice were sacrificed at day 32 with lung metastases were confirmed by histology.

Genomic southern blot of SL6 cells using an 1.3 kb neo fragment probe showed a single chromosomal integration of pLLGSV; both the reporter gene and the regulated promoter were faithfully duplicated in accordance with the retroviral life cycle. Northern blotting of poly(A) RNA isolated from SL6ΔT using a 550 bp fragment of 5' β-geo as a probe, showed a major transcript of 7 Kb in length, and two transcripts of 7.5 Kb and 6.5 Kb in smaller amount. Hybridization with the cloned gene confirmed that the 7 Kb and 6.5 Kb transcripts were fusion transcripts of the reporter gene and mRNA initiated at a chromosomally-located promoter external to the vector. During cDNA cloning (see below), we also isolated many alternatively spliced cDNA products, in which the splice acceptor site of the second copy of the reporter gene in the provirus had been spliced to several cryptic splice donors of the first reporter gene, and such aberrant splicing may result in multiple transcripts in Northern blots, as has been observed previously (Friedrich and Soriano, 1991, supra).

cDNA Cloning and Sequence Analysis

A biotin labeled oligodeoxyribonucleotide that corresponds to the 5' end of β-geo was used to select β-geo fusion mRNA from SL6ΔT cells by hybridization; the hybridized mRNAs were purified using streptavidin-coated paramagnetic particles, reverse transcribed, converted to double strand cDNA, cloned into the E. coli plasmid pAmp1, and sequenced by standard methods. The cloned 120 bp cDNA segment contained 70 bp of a novel sequence fused in frame to the splice acceptor site 5' to β-geo. A data base search using the BLAST program (Altschul et al., J. Mol. Biol. (1990) 215:403–410) showed 97% identity to a mouse partial cDNA sequence of unknown function identified by its expression during differentiation of F9 mouse embryonal carcinoma cells (Nishiguchi et al., (1994) J. Bio. Chem. 116:128–139.

A mouse NIH 3T3 cell cDNA library was screened with the 70 bp cDNA probe to obtain a full length gene. Four positive clones were isolated, and all contained a 1148 bp open translational reading frame (ORF) encoding a predicted 381 amino acid protein of 43,108 kDa. The gene defined by this sequence was designated as tumor susceptibility gene 101 (tsg101). A potential consensus sequence for initiation of translation, followed by an adenosine residue three bases upstream of a putative ATG translation start codon, was located near the 5' end of the tsg101. A splice donor consensus sequence (AG) was observed 72 nucleotides into the cDNA sequence analyzed and four codons downstream of the ATG.

The sequence of full length tsg101 cDNA and the predicted amino acid sequence of the Tsg101 protein were used to search the non-redundant DNA and protein sequence databases of the National Center for Biotechnology Information using the BLAST program. This analysis indicated that amino acids 231 to 301 of tsg101 are identical, except for two mismatches to cc2, an α-helix domain encoded by a partial cDNA clone identified by its ability to express a protein that interacts with stathmin (Maucuer et al., PNAS USA (1995) 92:3100–3104)—an evolutionarily-conserved phosphoprotein implicated in the integration and relay of diverse signals regulating cell growth (Sobel, Trends Biochem. Sci. (1991) 16:301–305). The algorithm of Stock and colleagues (Lupas et al., Science (1991) 252:1162–1164) predicts with a probability of ) 99.8% that the helical domain of Tsg101 will form a coiled-coil structure. A protein pattern search of full length Tsg101 identified a leucine zipper domain within the coiled-coil domain of Tsg101, consistent with the observed ability of the cc2 domain to interact with stathmin. Additionally, seven potential protein kinase C phosphorylation sites (aa11, 38, 85, 88, 215, 225, 357), five potential Casein kinase II phosphorylation sites (aa38, 210, 249, 265, 290), two potential N-myristorylation sites (aa55, 156), and three potential N-glycosylation sites (aa44, 150, 297) were present in Tsg101 (Bairoch and Bucher, Nucleic Acids Res. (1994) 22:3583–9). A protein motif search (Prints, Leads University, UK) showed that aa37–46 of Tsg101 resembles the helix-turn-helix signature domain of the bacteriophage λ repressor (i.e., HTHLAMBDA) (SEQ. ID No: 05) (Brennan and Matthews, J. Biol. Chem. (1989) 264:1903–1906), and that aa73–83 resembles a fungal Zn-cys bi-nuclear cluster signature (FUNGALZCYS) (SEQ. ID NO. 06) (Pan and Coleman, PNAS USA (1990) 87:2077–2081 ).

Expression of tsg101 Sense and Antisense RNA Cause Transformation of Naive NIH3T3 Cells To confirm the role of tsg101 in cell growth, we investigated the effects of overexpression of tsg101 in sense and antisense orientations in naive NIH 3T3 cells. In both instances, the tsg101 sequence was expressed in stably transfected cells under control of the cytomegalovirus (CMV) promoter. Expression of tsg101 in either the sense or antisense orientation resulted in transformation of naive NIH3T3 cells, as indicated by the ability to form colonies on 0.5% agarose. Whereas no colonies were observed in cells transfected with the vector lacking the insert or in mock transfected cells.

Experimental Procedures

Construction of Vectors

To construct the self-inactivated retroviral gene search vector pLLGSV, a 4.3 kb XhoI-XhoI fragment from pSAβ-geo (Friedrich and Soriano, Genes & Develop. (1991) 5:1513–1523), containing β-geo reporter gene and a splice acceptor sequence 5' to the reporter, was ligated into a XhoI linker site of pACYC184 plasmid (Chang and Cohen, J. Bacteriol. (1978) 134:1141–1156) that had been digested with Tth111I and XbaI. The NheI site of pACYC was then deleted and the XhoI site 5' to the β-geo reporter gene was converted into a NheI site by linker insertion; a 1.45 kb PvuII-StuI fragment containing 14 lac operator repeats and a SV40 minimal promoter sequence from pL14CAT (Labow et al., 1990, supra) was introduced into an SpeI 5' to the splice acceptor site and β-geo in the opposite orientation to β-geo. The polyadenylation signal of β-geo was deleted by XbaI digestion and replaced with a NheI linker. This 5.4 kb NheI—NheI fragment was then ligated in the same orientation as retroviral transcription, into a NheI site at the deleted 3' LTR of pHHAM (Hawley et al., PNAS USA (1987) 84:2406–2410) after NheI partial digestion.

The transactivator vector pLLTX was derived from pHC-MVLAP348 (Labow et al., Mol. Cell, Biol. (1990) 10:3343–3356). The HindIII site at the 3' end of the transactivator was first deleted and a 1952 bp SfiI fragment containing a HyTK gene expression cassette (Lupton et al., Mol. Cell. Biol. (1991) 11:3374–3378), was ligated into the HindIII site upstream of transactivator to yield pLAPHyTK. A 200 bp DNA fragment containing two directly repeated loxP sites derived from pBS30 (Sauer and Henderson, Nucleic Acids Res. (1989) 17:147–161) was introduced into a ClaI site of pLAPHyTK to give pLLTX. pBS30 was first digested with SalI and BamHI, and ligated with a HindIII linker; then the vector was digested with AatII and XhoI to generate this 200 bp fragment with two directly repeated loxP sites. This 200 bp fragment was ligated into a ClaI site of pLAPHyTK to give pLLTX.

To construct the expression vector pLLEXP I, a 1410 bp fragment [containing a human β-actin promoter, the puromycin resistance gene pac, and an SV40 poly(A) site] was first cloned into the BamH1 site of pBR332 to generate pBR-β-pac. The SfiI fragment containing the HyTK gene expression cassette (Lupton et al., 1991, supra) was then inserted into a BamHI site of pBR-β-pac, after BamHI partial digestion to give pBR-β-pac-HyTK. The expression vector pLLEXP I was generated by NheI and BglII digestion of pBR-β-pac-HyTK to remove the HyTK gene and replaced by cDNA inserts.

Cell Culture and Transfection NIH 3T3 cells (ATCC) and GP+E-86 cells (Markowitz et al., J. Virol. (1988) 62:1120–1124) were cultured in Dubecco's modified Eagle's medium (DMEM) supplemented with 10% calf serum (3T3) or 10% new born calf serum (GP+E-86), 100 U/ml penicillin, and 100 mg/ml streptomycin. DNA transfection was carried out by electroporation (Potter et al., PNAS USA (1984) 81:7161–7165) using Cell-Porator Electroporation systems I (Life Technologies, Inc.) and Lipofectamin (Life Technologies, Inc.) according to the protocol of the manufacturer.

Retroviral Infection of Mouse Fibroblast NIH3T3 Cells

To generate infectious retrovirus, pLLGSV was linearized by treatment with ScaI and transfected into helper cell line GP+E-86 by electroporation. The transfected GP+E-86 cells were replated on day 3 and selected with 800 µg/ml G418 for 2-3 weeks. All G418 resistant clones were isolated and expanded in 24-well plates. Culture supernatant from each clone was incubated with NIH 3T3 cells in the presence of polybrene (8 µg/ml) for 8 hr, and the frequency of integration behind the chromosomal promoter was subsequently determined by X-gal staining of the infected NIH 3T3 cells. The helper cell clones giving the highest frequency of integrations behind chromosomal promoters were expanded and culture supernatant was collected for large scale infection of NIH 3T3 cells.

Isolation of Transformed Clones and Tumorigenicity Assay

Cultures of G418 resistant NIH 3T3 cells were trypsinized and transfected with HindIII linearized pLLTX DNA by electroporation. The transfected cells were selected with 500 µg/ml of hygromycin for 12-18 days. All hygromycin resistant clones were plated into 0.5% agarose (Li et al., *J. Natl. Cancer Inst.* (1989) 81:1406-1412), 4 to 6 weeks later, the colonies formed in 0.5% agarose were isolated and expanded to cell lines. To assay the tumorigenicity of the transfected cells, $10^5$ cells were injected into nude mice (NIH nu/nu, female and 6 weeks of age) subcutaneously over the lateral thorax. The animals were examined twice weekly and sacrificed five weeks later. The neoplastic nature of local tumors and lung metastases were confirmed by histologic examination (Fidler, *Cancer Metastasis Rev.* (1986) 5:29-49).

cDNA Cloning and Screening of cDNA Library

A biotin labeled oligodeoxyribonucleotide (27 mer) that corresponds to the 5' end of the β-geo reporter gene was hybridized with polyadenylated mRNA from SL6ΔT cells, and captured with Streptavidin paramagnetic particles (Promega). The oligo-hybridized mRNA was eluted and reverse transcribed with a gene specific primer corresponding to a sequence located upstream of the biotin labeled oligo into first strands of cDNA. A uracil DNA glycosylase (UDG) cloning site (Booth et al., *Gene* (1994) 146:303-308) was incorporated into the gene specific primer to facilitate cDNA cloning. The first strand cDNA was then 3' tailed with (dG)n by terminal transferase, and converted into ds cDNA using a UDG-oligo d(c)$_{20}$ primer and DNA polymerase. The ds cDNAs were cloned into the UDG-cloning vector pAMP1 (Life Technologies, Inc.) and screened for fusion to β-geo. A 70 bp cDNA segment of novel sequence fused in frame to the splice acceptor site 5' to β-geo was used as a probe to screen a mouse NIH 3T3 cDNA library (Stratagene). Positive clones were sequenced with Sequenase 2.0 (USB) for both strands.

Southern and Northern Blot Analysis

Genomic DNA was isolated by standard procedure. Total RNA was isolated with RNA STAT-60 (TEL-TEST), and poly(A) mRNA was isolated with PolyATtract (Promega). Both DNA and RNA blots were probed with PCR generated single-stranded DNA probes.

It is evident that the subject invention will easily serve to identify other genes associated with the regulation of cell growth. Additionally, the subject invention can serve to identify other genes associated with other cellular functions.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. A method for inactivating multiple copies of a gene at an expressed random chromosomal locus of eukaryotic cells, comprising;

introducing into said eukaryotic cells a knockout DNA construct to produce a genetically modified cell mixture, said knockout DNA construct comprising at least (i) an agent regulated promoter ("TF promoter") oriented for RNA transcription in the opposite direction to (ii) a first positive selection marker coding sequence located 5' of said TF promoter, wherein a transactivation factor is provided extrinsic to said eukaryotic cells or intrinsic to said cells by introducing a transactivation DNA construct, said transactivation DNA construct comprising at least (i) a gene sequence for a second positive selection marker, and (ii) a gene sequence for said transactivation factor which binds to the transcription initiation region of said TF promoter to initiate RNA transcription, whereby an antisense RNA is produced of the sequence 5' of an integration site of said knockout DNA construct; and growing said genetically modified cell mixture in a selective medium to obtain selected genetically modified cells, said selected genetically modified cells being characterized by (i) expression of said first positive selection marker coding sequence resulting from said knockout DNA construct being integrated downstream of a promoter for said gene at said expressed random chromosomal locus and under its trnascriptional regulatory control, and, in the presence of said agent, or when present, (ii) expression of said second positive selection marker gene sequence resulting in production of transactivator factor, wherein the first copy of said gene at said expressed random chromosomal locus is inactivated by integration of said knockout DNA construct downstream of said promoter and any other similar genes are inactivated by said antisense RNA.

2. The method of claim 1, further including the steps of assaying said selected genetically modified cells for a change in cell phenotype associated with inactivating multiple copies of said gene at an expressed random chromosomal locus.

3. The method of claim 1, wherein said introducing step includes introducing said knockout and transactivation DNA constructs successively so that said knockout construct is introduced first to produce first genetically modified cells and said transactivation DNA construct is introduced later to produce second genetically modified cells.

4. The method of claim 3, wherein said knockout construct and said transactivation DNA construct comprise first and second positive selection markers, respectively, and said growing step includes growing said genetically modified cells which comprise said knockout construct in a first selective medium to obtain first selected cells expressing said first selection marker and growing said second genetically modified cells in a second selective medium to obtain second selected cells expressing both positive selection marker sequences.

5. The method of claim 1, wherein said knockout DNA construct further includes a splice acceptor sequence which is 5' in relationship to said positive selection marker coding region sequence.

6. The method of claim 5, wherein said splice acceptor sequence is 3' in relationship to said TF promoter.

7. The method of claim 1, wherein said transactivation factor includes a transcription activation domain and a DNA-binding domain, and said TF promoter includes a promoter sequence linked to multiple copies of a sequence which binds said DNA-binding domain, said DNA binding domain being exogenous to said eukaryotic cells.

8. The method of claim 7, wherein
said promoter sequence comprises a domain derived from a viral transcription regulatory protein gene and said DNA-binding domain is derived from the lac repressor protein, and said sequence which binds said DNA-binding domain includes multiple copies of the lac operator sequence.

9. The method of claim 8, wherein said viral regulatory protein is VP16, and said promoter is a minimal SV-40 promoter.

10. The method of claim 1, wherein said eukaryotic cells are human cells.

11. A method for selecting eukaryotic cells that have a defined phenotype, said method comprising:
introducing successively into said eukaryotic cells a knockout DNA construct and a transactivation DNA construct to produce a genetically modified cell mixture, said knockout DNA construct comprising at least (i) a transactivation factor responsive promoter ("TF promoter") oriented for RNA transcription in the opposite direction to (ii) a first positive selection marker coding sequence located 5' of said TF promoter; said transactivation DNA construct comprising at least (i) a gene sequence for a second positive selection marker, and (ii) a gene sequence for said transactivation factor which binds to the transcription initiation region of said TF promoter to initiate RNA transcription, and (iii) a negative selection marker gene sequence for monitoring excision of both said transactivation factor gene sequence and said negative selection marker gene sequence, which are delimited by two site-specific recombination sites,
whereby an antisense RNA is produced of the sequence 5' of an integration site of said knockout DNA construct; and
growing said genetically modified cell mixture in a selective medium to obtain selected genetically modified cells, said selected genetically modified cells being characterized by (i) expression of said first positive selection marker coding sequence resulting from said knockout DNA construct being integrated downstream of a promoter for an expressed random chromosomal locus and under its transcriptional regulation control, and (ii) expression of said second positive selection marker gene sequence, wherein a first copy of a gene at said expressed random chromosomal locus is inactivated by integration of said knockout construct downstream of said promoter and any other similar genes are inactivated by said antisense RNA.

12. The method of claim 11, including the additional steps of introducing into said genetically modified cells a recombinase expression construct comprising a recombinase gene sequence to produce cells stably expressing said recombinase gene, whereby introduction of said recombinase expression construct into said genetically modified cells results in the absence of antisense RNA production.

13. The method of claim 12, wherein said recombinase is the bacteriophage P1 cre protein, and the recombinase sites are lox sites.

14. A method for identifying genes in mammalian cells governing a phenotype, said method comprising;
introducing into said mammalian cells a knockout DNA construct to produce first genetically modified cells, said knockout DNA construct comprising at least (i) a transactivation factor responsive promoter ("TF promoter") oriented for RNA transcription in the opposite direction to (ii) a first positive selection marker coding sequence located 5' of said TF promoter, whereby said knockout DNA construct is integrated into the genome of said mammalian cell with expression of said first positive selection marker when said knockout DNA construct is downstream from an endogenous promoter and said first positive-selection marker coding sequence is in proper reading frame for expression;
selecting for said first genetically modified cells by means of said positive selection marker;
introducing into said first genetically modified cells a transactivation DNA construct, said transactivation DNA construct comprising at least (i) a gene sequence for a second positive selection marker, and (ii) a gene sequence for said transactivation factor which binds to a transcription initiation region of said TF promoter to initiate RNA transcription, whereby an antisense RNA is produced of the sequence 5' of the integration site of said knockout DNA construct, to produce second genetically modified cells;
growing said second genetically modified cells in a selective medium to obtain selected second genetically modified cells, said selected second genetically modified cells being characterized by (i) expression of said first positive selection marker coding sequence resulting from said knockout DNA construct being integrated downstream of said endogenous promoter at an expressed random chromosomal locus and under its transcriptional regulatory control, and (ii) expression of said second positive selection marker gene sequence, wherein a first copy of a gene at said expressed random chromosomal locus is inactivated by integration of said knockout construct downstream of said endogenous promoter and any other similar genes are inactivated by said antisense RNA;
screening said selected second genetically modified cells for said phenotype to provide phenotypic cells; and
identifying said gene at said expressed random chromosomal locus which is associated with said phenotype.

15. A method for identifying genes in mammalian cells governing susceptibility to tumorigenesis, said method comprising:
introducing into said mammalian cells a knockout DNA construct to produce first genetically modified cells, said knockout DNA construct comprising at least (i) a transactivation factor responsive promoter ("TF promoter") oriented for RNA transcription in the opposite direction to (ii) a first positive selection marker coding sequence located 5' of said TF promoter, whereby said knockout DNA construct is integrated into the genome of said mammalian cell with expression of said first positive selection marker when said knockout DNA construct is downstream from an endogenous promoter and said first positive selection marker coding sequence is in proper reading frame for expression;

selecting for said first genetically modified cells by means of said first positive selection marker;

introducing into said first genetically modified cells a transactivation DNA construct, said transactivation DNA construct comprising at least (i) a gene sequence for a second positive selection marker, and (ii) a gene sequence for said transactivation factor which binds to a transcription initiation region of said TF promoter to initiate RNA transcription, whereby an antisense RNA is produced of the sequence 5' of the integration site of said knockout DNA construct, to produce second genetically modified cells; and growing said second genetically modified cells in a selective medium to obtain selected second genetically modified cells, said selected second genetically modified cells being characterized by (i) expression of said first positive selection marker coding sequence resulting from said knockout DNA construct being integrated downstream of a promoter for said endogenous promoter at an expressed random chromosomal locus and under its transcriptional regulatory control, and, (ii) expression of said second positive selection marker gene sequence, wherein a first copy of a gene at said expressed random chromosomal locus is inactivated by integration of said knockout construct downstream of said endogenous promoter and any other similar genes are inactivated by said antisense RNA;

screening said selected second genetically modified cells for tumorigenic phenotype to provide tumorigenic phenotype cells; and identifying said gene at said chromosomal locus which is associated with susceptibility to tumorigenesis.

16. A method according to claim 15, wherein at least one of said TF promoter and gene sequence for said transactivation factor is flanked by consensus sequences recognized by a recombinase for excision of the sequence between said consensus sequences; and including the additional steps of:

introducing said recombinase into said selected second genetically modified cells, whereby at least one of said TF promoter and gene sequence for said transactivation factor is excised; and screening said selected second genetically modified cells for tumorigenic phenotype;

whereby absence of tumorigenic phenotype of said selected second genetically modified cells wherein at least one of said TF promoter and gene sequence for said transactivation factor was excised indicates that the gene at said locus is associated with susceptibility to tumorigenesis.

17. A knockout DNA construct sequence comprising a promoterless positive selection marker coding sequence and a promoter responsive to a transactivation factor located 5' of said coding sequence and oriented for transcription in the direction opposite said coding sequence.

18. A knockout vector comprising the DNA sequence of claim 17.

19. A transactivation DNA construct sequence comprising a gene sequence for a transactivation factor, a gene sequence for a positive selection marker, and a gene sequence for a negative selection marker, said gene sequence for a transactivation factor and said gene sequence for said negative selection marker being delimited by two site-specific recombination sites.

20. A transactivation vector comprising the DNA sequence of claim 19.

21. A eukaryotic cell having integrated at a random chromosomal locus in the genome a DNA sequence comprising a promoterless positive selection marker coding sequence and a promoter responsive to a transactivation factor located 5' of said coding sequence and oriented for transcription in the direction opposite said coding sequence.

22. The eukaryotic cell of claim 21, further comprising an expression construct comprising a gene encoding said transactivation factor.

23. A method for establishing a function for a gene in mammalian cells for which at least a partial sequence is known, said method comprising;

introducing into said mammalian cells a knockout DNA construct to produce a genetically modified cell mixture, said knockout DNA construct comprising at least (i) a transactivation factor responsive promoter ("TF promoter") oriented for RNA transcription in the opposite direction to (ii) a first positive selection marker coding sequence located 5' of said TF promoter and (iii) homologous recombination sites that delimit said TF promoter and said positive selection marker coding region sequence to allow for integration of said TF promoter and said selection marker coding region sequences into a coding region of said known gene, and (iv) a gene sequence for said transactivation factor for binding to said transcription initiation region sequence responsive to said transactivation factor;

growing said genetically modified cell mixture in a selective medium to select for cell integrants being characterized by (i) expression of said first positive selection marker coding sequence resulting from said knockout DNA construct being integrated into a coding region of said known gene and under its transcriptional regulation control; and assaying said cell integrants for a change of phenotype associated with introducing said knockout construct.

* * * * *